US010105178B2

(12) United States Patent
Calabro' et al.

(10) Patent No.: US 10,105,178 B2
(45) Date of Patent: Oct. 23, 2018

(54) ESOPHAGEAL PROBE WITH THE TEMPERATURE CHANGE SPEED DETECTION SYSTEM

(71) Applicant: FIAB S.P.A., Vicchio (FI) (IT)

(72) Inventors: Alberto Calabro', Florence (IT); Antonio Fasano, Florence (IT)

(73) Assignee: FIAB S.P.A., Vicchio (IT)

( * ) Notice: Subject to any disclaimer, the term of this patent is extended or adjusted under 35 U.S.C. 154(b) by 133 days.

(21) Appl. No.: 15/267,257

(22) Filed: Sep. 16, 2016

(65) Prior Publication Data
US 2017/0086919 A1 Mar. 30, 2017

(30) Foreign Application Priority Data

Sep. 30, 2015 (IT) .................. 102015000056858

(51) Int. Cl.
A61B 18/14 (2006.01)
A61B 5/01 (2006.01)
A61B 18/02 (2006.01)
A61B 5/00 (2006.01)
A61B 17/00 (2006.01)
A61B 18/12 (2006.01)
A61B 18/00 (2006.01)

(52) U.S. Cl.
CPC ............ *A61B 18/1492* (2013.01); *A61B 5/01* (2013.01); *A61B 18/02* (2013.01); *A61B 5/6852* (2013.01); *A61B 18/12* (2013.01); *A61B 2017/00101* (2013.01); *A61B 2017/00123* (2013.01); *A61B 2018/00577* (2013.01); *A61B 2018/00797* (2013.01); *A61B 2018/00964* (2013.01); *A61B 2018/00988* (2013.01); *A61B 2018/0212* (2013.01)

(58) Field of Classification Search
CPC ...... A61B 18/1492; A61B 2018/00964; A61B 5/01; A61B 5/0421; A61B 18/02; A61B 2018/00577; A61B 2018/00797; A61B 2018/00988; A61B 18/12; A61B 2017/00101; A61B 2017/00123; A61B 2018/0212
See application file for complete search history.

(56) References Cited

U.S. PATENT DOCUMENTS

| 5,730,720 A * | 3/1998 | Sites ..................... A61M 1/369 604/27 |
| 2002/0151880 A1* | 10/2002 | Lafontaine ............. A61B 18/02 606/21 |
| 2005/0222556 A1 | 10/2005 | Shigeki et al. |
| 2006/0069385 A1* | 3/2006 | Lafontaine ............. A61B 18/02 606/21 |
| 2007/0239062 A1* | 10/2007 | Chopra ................... A61B 5/01 600/549 |
| 2008/0177180 A1* | 7/2008 | Azhari ................. A61B 8/0825 600/439 |

(Continued)

Primary Examiner — Sean Dougherty
(74) Attorney, Agent, or Firm — Pearne & Gordon LLP

(57) ABSTRACT

The present invention has for object a device (1) for detecting the temperature of the esophagus (E) in cardiac ablation treatments which device, unlike known devices, allows to more securely monitor the temperature of the esophageal lumen, thereby promptly detecting any possible criticality to which the patient (P) may be exposed due to excessively rapid temperature fluctuations.

11 Claims, 2 Drawing Sheets

(56) References Cited

U.S. PATENT DOCUMENTS

Figure 1:
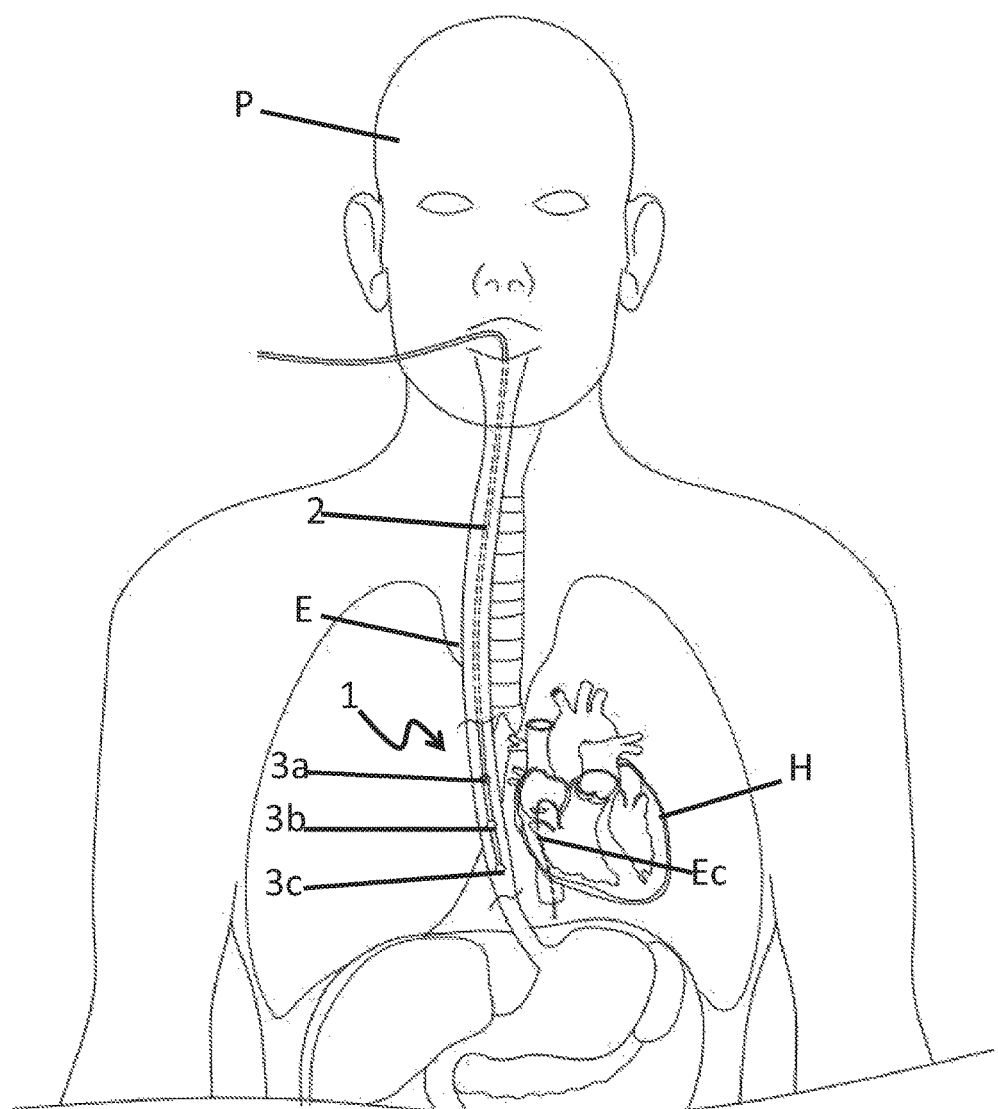

| | | | |
|---|---|---|---|
| 2009/0024023 A1* | 1/2009 | Welches | A61B 18/201 |
| | | | 600/424 |
| 2010/0168624 A1 | 7/2010 | Sliwa | |
| 2011/0010115 A1* | 1/2011 | Bosshart | G01M 3/002 |
| | | | 702/51 |
| 2013/0023772 A1* | 1/2013 | Kinsley | A61B 5/01 |
| | | | 600/474 |
| 2013/0211283 A1* | 8/2013 | Bunch | A61B 5/6853 |
| | | | 600/549 |
| 2013/0245457 A1* | 9/2013 | Kinsley | A61B 5/01 |
| | | | 600/474 |
| 2015/0105687 A1* | 4/2015 | Abreu | A61B 5/01 |
| | | | 600/549 |
| 2015/0105701 A1* | 4/2015 | Mayer | A61M 16/14 |
| | | | 601/3 |
| 2015/0119868 A1* | 4/2015 | Lalonde | A61B 18/02 |
| | | | 606/21 |
| 2015/0328474 A1* | 11/2015 | Flyash | A61B 18/1233 |
| | | | 601/2 |
| 2016/0143630 A1* | 5/2016 | Pardey | A61B 10/0012 |
| | | | 600/549 |
| 2016/0228175 A1 | 8/2016 | Sliwa | |
| 2016/0262820 A1* | 9/2016 | Allison | A61B 18/02 |
| 2017/0086919 A1* | 3/2017 | Calabro' | A61B 18/1492 |
| 2017/0143258 A1* | 5/2017 | Calabro' | A61B 5/01 |
| 2017/0281270 A1* | 10/2017 | Masuda | A61B 18/1492 |

* cited by examiner

ESOPHAGEAL PROBE WITH THE TEMPERATURE CHANGE SPEED DETECTION SYSTEM

The invention has for an object a device for the measurement and monitoring of the temperature of the esophageal lumen in cardiac ablation treatments for the treatment of atrial fibrillation, which device allows to carry out such monitoring with safer mode compared to currently known devices, particularly enabling effective prevention of thermal damage to the esophagus and other neighboring organs, such as the phrenic nerve. Unlike known devices, the present invention more generally permits to more securely monitor the temperature of those parts of the patient's body resulting to be more critical from a thermal viewpoint in the course of such treatments.

Cardiac ablation is intended to locally destroy the electrically active tissues affected by the disease responsible for the detected arrhythmia.

Cardiac ablation treatments occur by heating or cooling. In the first case a special catheter is used, which is provided with an electrode emitting a radio frequency electromagnetic field. In the second case, in which the ablation treatment is also called cryo-ablation, a balloon is used that is inflatable with a gas at a very low temperature. During cardiac ablation treatments it is extremely important to monitor the temperature of the tissue surrounding the area where destruction of pathological tissues is being effected because, due to excessive heat or cooling, the surrounding tissues might be damaged in a severe and even lethal manner. In particular, it was found that the esophagus is a potentially at risk organ for the fact that its anatomical arrangement can be very proximate to the left atrial posterior wall being an area usually placed next to the ablation sites.

The devices known at present comprise at least a probe provided with thermal sensors that may be variable in number and type. This probe is adapted to be inserted into the esophagus of the patient, and so positioned as to be able to sense the temperature in the most critical points. Such probe preferably comprises an esophageal catheter, whereon such sensors are arranged.

These sensors are connected to a system capable of generating a visual and/or acoustic signal when the maximum or minimum temperature respectively of the patient's esophagus reaches a preset threshold deemed safe for the patient. During ablation treatments, the esophagus temperature may however vary very rapidly, which implies that the previously mentioned signal may be insufficient to prevent the esophagus temperature from reaching levels which may result in very serious damages to the patient. The temperature can vary rapidly indeed, such as to reach very critical values even in the short timeframe in which the ablation procedure is suspended. This circumstance is particularly evident even for cryo-ablation proceedings being often characterized by severe changes in temperature. Additionally, even after that the ablation procedure is interrupted, the variation of the temperature continues by inertia in a manner all the more marked the higher is the temperature variation speed upon interrupting the ablation procedure.

It is an object of the present invention to develop a device for the measurement and monitoring of the temperature in the esophagus during cardiac ablation treatments, which, unlike known devices, allows to increase the level of safety during treatment, thereby promptly detecting any possible criticality to which the patient may be exposed that may arise from excessively rapid temperature fluctuations.

In particular, object of the present invention is to develop a device for the measurement and monitoring of the temperature in the esophagus during cardiac ablation treatments which, unlike known devices, is capable of promptly signaling a risk situation arising from improper esophagus temperature, possibly well before a threshold value thereto related is reached.

This object is attained by a device for the detection and monitoring of the temperature in the esophagus during cardiac ablation treatments comprising an esophageal probe insertable into the esophagus of a patient, and at least one sensor disposed on said probe and suitable to detect the temperature of a respective portion of said esophagus. Such device may be characterized by one or more of the characteristics described in the appended claims.

Such at least one sensor is configured to generate, in successive time instants, respective detection signals indicative of said temperature.

The device further comprises a control unit connectable in use to said probe, preferably by one or more connectors or other connecting means.

The control unit is configured to receive said detection signals from said at least one sensor, for example, by one or more connectors or other connecting means.

The control unit is programmed with at least one preset temperature limit value. This temperature limit value corresponds to a maximum or minimum temperature value reachable by said respective portion of the esophagus.

Hence, this temperature limit value reflects the preset thermal threshold for the possible interruption of the ablation procedure.

Such at least one temperature limit value can be set and stored in the control unit by a user.

The control unit is configured to calculate, for each of said instants, a variation speed of said temperature.

The control unit is configured to calculate said speed, preferably at least partially as a function of said detection signals.

Preferably the control unit is configured to calculate said temperature variation speed for each of said instants by calculating the first derivative, or approximation thereof, of the temperature values detected by said at least one sensor.

This approximation may for example be calculated as the ratio between the temperature variation within a certain time interval and the time interval itself.

Furthermore, in order to calculate this speed, the control unit may advantageously use those temperature values resulting from averages that were calculated based on the actual values detected by said at least one sensor in more respective instants, in order that one or more frequency components may be removed and/or filtered, which characterize temperature temporal fluctuation and which are anyhow originated from disturbances.

The control unit is configured to determine, for each of said instants, a value of the residual time required to reach said at least one temperature limit value by said respective portion of the esophagus.

The control unit is configured to calculate said residual time value, preferably as a function of said temperature variation speed of said respective portion of the esophagus.

The device is configured to provide on output, for each of said instants, at least one information correlated to the residual time value required to reach said temperature limit value by said respective portion of the esophagus.

In a particular embodiment of the present invention, said at least one information comprises an acoustic and/or luminous signaling.

For the purpose of transmitting said at least one information to the user, said device preferably comprises at least one acoustic and/or luminous signal giver. Said signal giver is adapted to be activated so as to generate said signaling.

The control unit is preferably configured to emit at least one activation signal capable of activating said acoustic and/or luminous signal giver.

Moreover, this control unit is preferably configured to emit such activation signal when said variation speed is equal to or greater than a preset threshold value, or when said residual time value calculated is equal to or lower than a preset threshold value.

Preferably such threshold values may be set and stored in the control unit by a user.

This signal then is adapted to warn the user with respect to the achievement, by said respective portion of the esophagus, of the preset thermal threshold value and/or residual time value.

It should be appreciated that, even when said temperature variation speed of the respective portion of the esophagus and/or said residual time go beyond such threshold values, at least one information is transmitted by the device. Indeed, the presence of said signal giver remaining in a deactivated condition, is in this case indicative of the fact that the values of these critical variables are within the preset limits.

In order to receive the activation signal, the signal giver is preferably connected to said control unit, for example, via one or more connectors or other connecting means. This signal giver may further be placed on the control unit and/or integrated therein.

Said at least one information may also or alternatively include at least one viewing of said residual time value and temperature speed variation value.

Advantageously, the device may comprise a viewer configured for viewing the numeric value of the values of these critical variables.

This viewer is preferably connected to said control unit, for example via one or more connectors or other connecting means. Such viewer may further be placed on the control unit and/or integrated therein.

Such information may also or alternatively include at least viewing the evolution in time of said temperature or said residual time value as well as variation speed.

Preferably said at least one sensor is associated with at least a transducer for generating at least said detection signals.

In a possible embodiment of the present invention, the device comprises two or more temperature sensors disposed on said probe. Said sensors are adapted to detect the temperature of a plurality of respective portions of said esophagus.

Each of said sensors is configured to generate, in successive time instants, respective detection signals that are indicative of the temperature of the corresponding esophagus portion.

The control unit is adapted to receive the detection signals from each of said sensors.

The control unit is configured to calculate, for each of said sensors and for each of said instants, a temperature speed variation of the corresponding esophagus portion.

The control unit is configured to determine, for each of said sensors and for each of said instants, a corresponding residual time value which is required to reach said temperature limit value by the respective portion of the esophagus.

The device is further configured to provide on output, to one or more of said sensors and for each of said instants, at least one respective information related to the residual time value required to achieve said temperature limit value by the respective portion of the esophagus.

For each of said sensors, said control unit is configured for calculating said temperature variation speed of the corresponding esophagus portion at least partially on the basis of the detection signals coming from the respective sensor.

For each of said sensors, said control unit is configured to calculate said residual time value required to achieve said temperature limit value by the respective portion of the esophagus as a function of the respective temperature variation speed of said respective esophagus portion.

This temperature variation speed is preferably the one previously calculated.

Such viewer, where present, may be configured for viewing, among all the residual time values calculated for said sensors, only the numerical value of the residual time with a lower entity.

Preferably said probe comprises a catheter.

Preferably said catheter is free of any ablators.

Preferably said sensors are distributed along a prevalent direction of development of said probe and/or of said catheter.

According to a further aspect, the present invention relates to a device for detecting the temperature in the esophagus in the course of cardiac ablation treatments, comprising an esophageal probe insertable into the esophagus of a patient, and comprising two or more temperature sensors disposed on said probe and adapted to detect the temperature of several respective portions of said esophagus, each of said sensors being configured to generate, in successive time instants, respective detection signals indicative of the temperature of the corresponding portion of the esophagus.

Said device further comprises a control unit (C) that is connectable in use to said probe for receiving the detection signals from each of said sensors.

The device is characterized in that said control unit is programmed with a temperature variation speed limit value and is configured to calculate, for each of said sensors and for each of said instants, and at least partially on the basis of the detection signals received from the respective sensor, a respective variation speed of said temperature, said device being configured to provide on output, to one or more of said sensors and for each of said instants, at least one information correlated to said respective temperature speed variation of the corresponding portion of the esophagus.

Said at least one information comprises an acoustic and/or luminous signaling and said device comprises at least one acoustic and/or luminous signal giver suitable to generate said signaling.

Said control unit is configured to emit at least one activation signal suitable to activate said acoustic and/or luminous signal giver when said respective temperature speed variation of the respective sensor is equal to or higher than said speed limit value.

The characteristics of the present invention will become more apparent in the following detailed description of the more general claimed technical concepts illustrated by way of non-limiting example.

Figure 2:
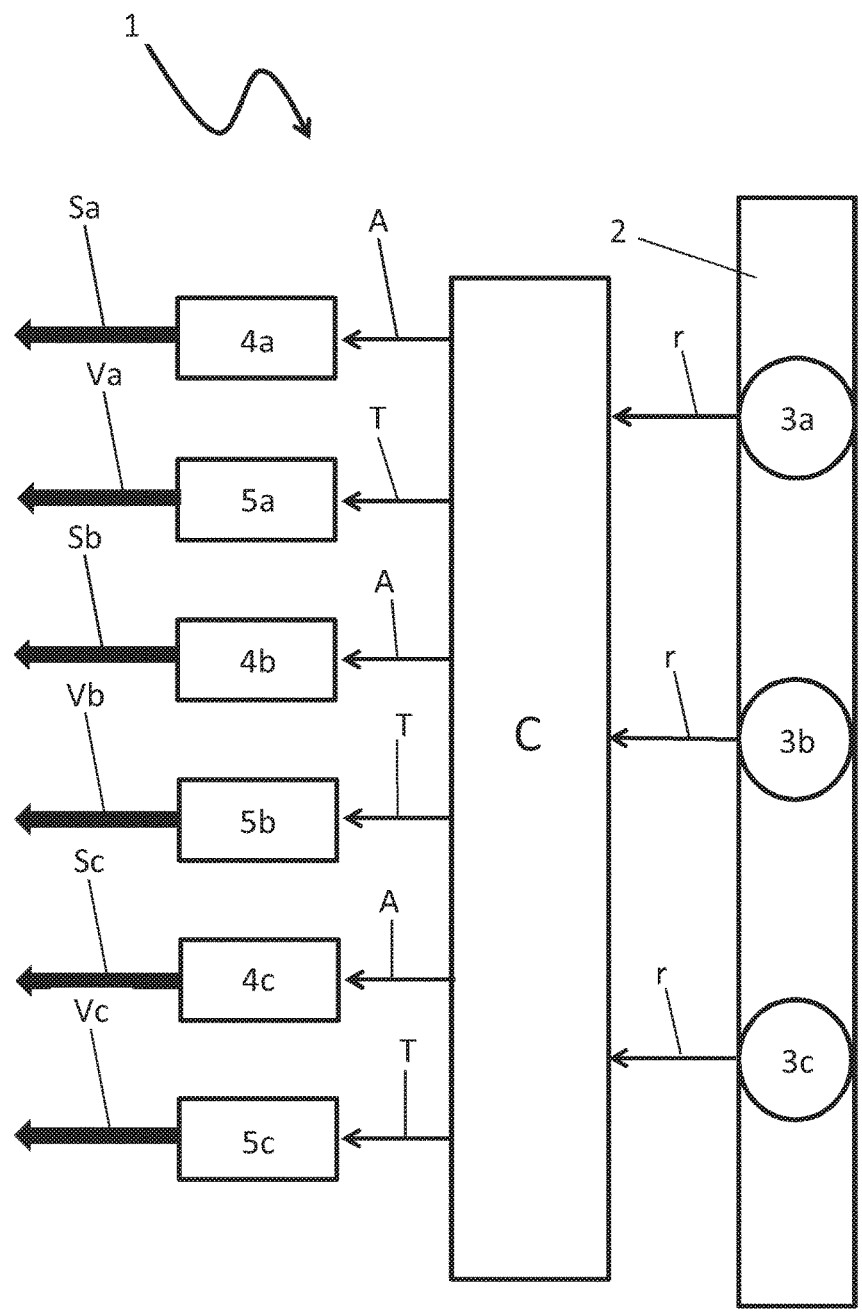

The following detailed description refers to the appended drawings wherein:

FIG. 1 shows a part of a particular embodiment of the present invention in a possible condition of use;

FIG. 2 schematically illustrates how the present invention operates.

In FIG. 1 it is shown a device 1 for measuring and monitoring the temperature of the esophagus E in the course of cardiac ablation treatments, according to a particular embodiment of the present invention.

The device 1 comprises an esophageal probe, which in turn comprises advantageously, in the embodiment illustrated, an esophageal catheter 2 insertable into the esophagus E of a patient P.

The attached figures refer to a specific condition of use during which an electro-catheter Ec is inserted in the heart H of a patient P. In the detailed description of herein, this electro-catheter Ec is not to be confused with the catheter 2 belonging to the device 1.

In the condition of use depicted in FIGS. 1 and 2, the electro-catheter Ec serves to remove, by heating, the pathological tissue responsible for anomalies in the patient's P heart rhythm.

The present invention however also applies in the case of cardiac ablation treatment occurring by cooling, also termed cryo-ablation treatment.

The Ec electro-catheter operates preferably on the inner surfaces of the heart H left atrium of the patient P.

In the specific embodiment herein illustrated, the device 1 comprises three temperature sensors 3a, 3b and 3c disposed on said catheter 2. The number of sensors may be different from that of the embodiment shown.

The number of sensors of the illustrated embodiment is to be considered for purposes of example only.

In the embodiment depicted, the catheter 2 is advantageously devoid of any ablators.

Each of the sensors 3a, 3b and 3c is suitable to detect the temperature of a respective portion of said esophagus E. These portions of the esophagus E belong to the esophageal region which, in the illustrated use condition, is most involved in temperature increase resulting from Ec electro-catheter activities.

In the embodiment shown, the sensors 3a, 3b and 3c are arranged along the catheter 2 in order to sense the temperature of respective different portions of the esophagus E. In addition, in the embodiment shown, the sensors 3a, 3b and 3c are distributed along a major extension direction of the catheter 2.

The arrangement of the sensors 3a, 3b and 3c along the catheter 2 is further visible in FIG. 2.

Each of these sensors 3a, 3b and 3c, is configured to generate, at successive instants, respective detection signals indicative of the temperature of the corresponding portion of the esophagus E. These detection signals are indicated in FIG. 2 by the arrows r.

Preferably each of said sensors 3a, 3b and 3c is associated with at least a respective transducer, not shown, for generating at least said detection signals r. The assembly of at least one sensor and at least one transducer may then be defined as a temperature detector.

Such detector may comprise for example at least one conductor or several conductors adapted to be subjected to a difference in potential indicative of the detected temperature.

The device 1 further comprises a control unit C that is connectable in use to said catheter 2. The control unit C is adapted to receive, via non-illustrated connecting means, for example by way of one or more connectors, the detection signals r coming from each of the sensors 3a, 3b and 3c.

The box C of FIG. 2 is a block, which schematically illustrates the control unit C. The same FIG. 2 is illustrative of the shape of the catheter 2, at least in relation to the positioning of the sensors 3a, 3b and 3c.

The control unit C is programmed with at least one temperature limit value reachable by the esophagus E. This temperature limit value can be set and stored in the control unit C by a user.

In the use condition shown in FIG. 1, this temperature limit value is a maximum value, in that the electro-catheter Ec is capable of carrying out a cardiac ablation treatment occurring by heating.

In a further use condition, wherein the treatment may be a cryo-ablation treatment, i.e. an ablative treatment occurring by cooling, this temperature limit value might be a minimum value.

For each of the sensors 3a, 3b and 3c, the control unit C is configured to calculate, within or in respect to each of said time instants, a temperature speed variation of the corresponding portion of the esophagus E. The respective portion of which the control unit C is calculating the temperature variation speed may therefore, in the specific case referred to by the appended figures, be a portion of the esophagus E associated to the sensor 3a, to the sensor 3b or to the sensor 3c.

For each of the sensors 3a, 3b and 3c, the control unit C is advantageously configured to perform the calculation of the respective temperature variation speed, at least partially as a function of the detection signals r coming from the respective sensor 3a or 3b or 3c.

For each sensor 3a or 3b or 3c, the control unit C is advantageously so configured as to be able to filter and/or eliminate the frequency components related to disorders in the temporal evolution of temperature of the corresponding portion of the esophagus E, for example by attributing to a certain instant, an average temperature calculated as the average among the values actually observed in several respective instants.

In FIG. 2 the passage of detection signals r from the sensors 3a, 3b and 3c to the central unit C is shown schematically by the arrows r, which therefore indicate in general both these detection signals r and the passage thereof from the sensors 3a, 3b and 3c to the control unit C.

For each of the sensors 3a, 3b and 3c, the control unit C is configured to determine, within or is respect to each of said time instants, a residual time value required to reach said temperature limit value by the respective portion of the esophagus E.

For each of said sensors 3a, 3b and 3c, said central unit C is advantageously configured to perform calculation of said residual time value as a function of the respective temperature variation speed.

The latter speed can advantageously be that previously calculated by the control unit C for the respective sensor 3a or 3b or 3c and for the same time instant.

In other words, for each of the sensors 3a, 3b and 3c and for each of these instants, the control unit calculates an approximation of the temperature variation speed of the respective portion of the esophagus E and, based on said speed, the estimated residual time for reaching the temperature limit value by that respective portion.

In the embodiment shown, for each time instant, the control unit C calculates three residual time values. Each of said three residual time values is then associated with a respective portion of the esophagus and to the respective sensor 3a or 3b or 3c.

For each of said instants and for each of the sensors 3a, 3b and 3c, the control unit C is configured to calculate the temperature variation speed by calculating the first temporal derivative or approximation thereof of the temperature of the corresponding esophagus E portion.

In particular, the calculation of the first temporal derivative approximation of the temperature of the corresponding esophagus E portion may be based on the ratio between the difference existing between at least two temperature values detected by the respective sensor 3a or 3b or 3c, and the temporal distance between the instants associated with said at least two values respectively.

The device 1 is further configured to provide on output, for one or more of said sensors 3a, 3b and 3c and for each of said instants, at least one respective information. Such at least one respective information is related to the residual time value required to achieve said temperature limit value by the respective portion of the esophagus E.

In the embodiment shown, said at least a respective information, for each of said sensors 3a, 3b and 3c, may comprise an acoustic and/or luminous signaling. This signaling is illustrated in FIG. 2 by an arrow denoted by Sa for the sensor 3a, by an arrow Sb for the sensor 3b and by an arrow Sc for the sensor 3c.

To this end, the device 1 comprises, for one or more of said sensors 3a, 3b and 3c, at least one acoustic/luminous signal giver 4a or 4b or 4c. The signal giver 4a or 4b or 4c is suitable to generate a respective signaling Sa or Sb and Sc.

For each of said sensors 3a, 3b and 3c, the control unit C is configured to emit at least one activation signal A suitable for activating at least one respective signal giver 4a or 4b or 4c. The control unit C is configured to emit said at least one activation signal in at least three circumstances: the temperature has reached the preset threshold value, the temperature variation speed has reached the preset threshold value, the residual time value required to achieve that temperature limit value by the respective portion of the esophagus E, is equal to or lower than a preset threshold value.

These threshold values can be set and stored in the control unit C by a user.

Such at least one activation signal A is represented in FIG. 2 by at least one arrow A which also indicates passage thereof from the control unit C to the respective signal giver 4a or 4b or 4c.

In the embodiment shown, several signal givers 4a 4b and 4c are depicted, each of which is functionally associated with a respective sensor 3a or 3b or 3c. The control unit C, in the embodiment shown, is therefore capable of sending more activation signals A, each of which can activate a respective signal giver 4a or 4b or 4c on the basis of the calculated residual time value required to reach said temperature limit value by the respective portion of the esophagus E.

Each of the signal givers 4a or 4b or 4c is preferably connected to the control unit C via connecting means (not shown), for example via one or more connectors. Each of these signal givers 4a or 4b or 4c may further be physically integrated in the control unit C, and/or disposed on the same control unit C, and/or fitted thereon.

Said at least one information may further or alternatively comprise, for each of the sensors 3a, 3b and 3c, viewing said calculated residual time value required to reach said temperature limit value by the respective portion of the esophagus E. Such viewing is indicated in FIG. 2 by an arrow referred to with Va for the sensor 3a, by an arrow Vb for the sensor 3b and by an arrow Vc for the sensor 3c.

To this end the device 1 comprises, for one or more of said sensors 3a, 3b and 3c, at least one viewer 5a, 5b or 5c. Each of the viewer 5a, 5b and 5c is suitable to generate a respective viewing Va or Vb or Vc.

In the embodiment shown there are multiple viewers 5a, 5b and 5c, each of which suitable to then view the numerical value of said residual time value required to achieve said temperature limit value by the respective portion of the esophagus E, of which the respective sensor 3a or 3b or 3c, associated with the respective viewer 5a or 5b or 5c detects the temperature.

According to a further possible embodiment there may be provided, by way of example, a single viewer that is suitable to view the lowest residual time value among all those calculated by the control unit C for the esophagus portions of which, the respective sensors 3a, 3b and 3c detect the temperature.

For the sake of completeness, FIG. 2 further depicts additional arrows T, which are an example of the further signals T that can be emitted by the control unit C. Such additional T signals are used by the viewer 5a or 5b or 5c to view temperature, temperature variation speed and residual time value associated with the respective sensor 3a or 3b or 3c.

Each of the viewers 5a or 5b or 5c is preferably connected to the control unit C via connecting means not shown, for example via one or more connectors. Each of those viewers 5a or 5b or 5c may also be physically integrated in the control unit C, and/or disposed on the same control unit C, and/or fitted thereon.

For one or more of the sensors 3a, 3b and 3c, such at least one information may further or alternatively comprise viewing of the evolution in time of said temperature detected by the respective sensor 3a or 3b or 3c, or of said time residual value required to achieve said temperature limit value by the respective portion of the esophagus 3.

This information may further or alternatively comprise the numerical value of the temperature detected by each sensor 3a or 3b or 3c.

It should be appreciated that, in other possible embodiments, the number of viewers 5a, 5b and 5c and/or the number of signal givers 4a, 4b and 4c may differ from that shown. The number of viewers or signal givers may also differ from the number of sensors 3a, 3b and 3c.

The invention attains the intended aim, and unlike the devices currently known, it makes available a device capable of controlling with a greater safety margin the temperature of the esophageal lumen in the course of cooling or heating cardiac ablation treatments.

This device may also be easily set in order that the limit temperature and/or said safety margin can be varied as a function of any particular needs.

The invention claimed is:

1. A device for detecting the temperature of the esophagus in cardiac ablation treatments,
   comprising an esophageal probe insertable into the esophagus of a patient, and
   at least one sensor disposed on said probe and suitable to detect the temperature of a respective portion of said esophagus,
   said at least one sensor being configured to generate, in successive time instants, respective detection signals indicative of said temperature,
   wherein said device further comprises a control unit connectable in use to said probe for receiving said detection signals from said at least one sensor and programmed with at least one preset temperature limit value reachable from said respective portion of the esophagus, characterized in that said control unit is configured to calculate, for each of said instants and at least partially as a function of said detection signals, a variation speed of said temperature, and to determine, for each of said instants and as a function of said temperature variation speed of said respective portion of the esophagus, a residual time value required to achieve said at least one temperature limit value by said respective portion of the esophagus, said device being further configured to provide on output, for each of said instants, at least one information correlated to the residual time value required to achieve said temperature limit value by said respective portion of the esophagus, and at least one further information correlated to the value of said temperature variation speed of said respective portion of the esophagus.

2. A device according to claim 1, wherein said at least one further information comprises an acoustic and/or luminous signaling and said device comprises at least one acoustic and/or luminous signal giver suitable to generate said signaling, and wherein said control unit is configured to emit at least one activation signal suitable to activate said acoustic and/or luminous signal giver when said calculated residual time value is equal to or lower than a preset threshold value, said threshold value being able to be set and stored in the control unit by a user.

3. A device according to claim 1, wherein said at least one information comprises a viewing of said residual time value and said device comprises at least one viewer configured for viewing a numerical value of said residual time.

4. A device according to claim 1, wherein said control unit is configured to calculate said temperature variation speed for each of said instants by calculation of a first derivative or approximation thereof of the temperature values detected by said at least one sensor.

5. A device according to claim 1, comprising two or more temperature sensors disposed on said probe and adapted to detect the temperature of several respective portions of said esophagus, each of said sensors being configured to generate, in successive time instants, respective detection signals indicative of the temperature of the corresponding portion of the esophagus, wherein said control unit is adapted to receive the detection signals from each of said sensors, wherein said control unit is configured, for each of said sensors and for each of said instants, to calculate a temperature variation speed of the corresponding portion of the esophagus and to determine a corresponding residual time value required to reach said temperature limit value by the respective portion of the esophagus, said device being further configured to provide on output, for one or more of said sensors and for each of said instants, at least one respective information related to the residual time value required to achieve said temperature limit value by the respective portion of the esophagus.

6. A device according to claim 5, wherein said at least one information comprises a viewing of said residual time value and said device comprises at least one viewer configured for viewing the numerical value of said residual time, wherein said viewer is configured to view, among all the residual time values calculated for said sensors, only the numerical value of the residual time of lower entity.

7. A device according to claim 5, wherein, for each of said sensors, said control unit is configured for calculating said temperature variation speed of the corresponding portion of the esophagus, at least partially as a function of the detection signals coming from the respective sensor, and wherein, for each of said sensors said control unit is configured to calculate said residual time value required to achieve said temperature limit value by the respective portion of the esophagus as a function of the respective variation speed of the previously calculated temperature.

8. A device according to claim 5, wherein said probe comprises a catheter.

9. A device according to claim 1, wherein said at least one temperature limit value can be set and stored in the control unit by a user.

10. A device according to claim 1, wherein said probe is devoid of any ablators.

11. A device according to claim 1, wherein said at least one sensor is associated with at least a transducer for generating at least said detection signals.

* * * * *